United States Patent
Venkatasubbarao et al.

(10) Patent No.: US 7,023,547 B2
(45) Date of Patent: Apr. 4, 2006

(54) APPARATUS INCLUDING A BIOCHIP FOR IMAGING OF BIOLOGICAL SAMPLES AND METHOD

(75) Inventors: Srivatsa Venkatasubbarao, Torrance, CA (US); Lothar U. Kempen, Redondo Beach, CA (US)

(73) Assignee: Maven Technologies, LLC, Los Angeles, CA (US)

( * ) Notice: Subject to any disclaimer, the term of this patent is extended or adjusted under 35 U.S.C. 154(b) by 716 days.

(21) Appl. No.: 09/838,700

(22) Filed: Apr. 19, 2001

(65) Prior Publication Data

US 2002/0021443 A1   Feb. 21, 2002

Related U.S. Application Data

(63) Continuation-in-part of application No. 09/614,503, filed on Jul. 7, 2000, now Pat. No. 6,594,011.

(51) Int. Cl.
*G01J 4/00* (2006.01)
*G01N 33/557* (2006.01)

(52) U.S. Cl. .................. 356/369; 356/445; 436/517; 436/805

(58) Field of Classification Search ........ 356/364–369, 356/445–448; 435/6, 7.1, 91.1; 436/524–528, 436/517, 805
See application file for complete search history.

(56) References Cited

U.S. PATENT DOCUMENTS

| | | | |
|---|---|---|---|
| 4,238,565 A | 12/1980 | Hornby et al. ........... 435/7 |
| 4,256,834 A | 3/1981 | Zuk et al. ............... 435/7 |
| 4,508,832 A | 4/1985 | Carter et al. | |
| 5,164,589 A | 11/1992 | Sjoedin | |
| 5,229,833 A | 7/1993 | Stewart | |
| 5,234,769 A * | 8/1993 | Shevlin ................ 428/409 |
| 5,255,075 A | 10/1993 | Cush | |
| 5,313,264 A | 5/1994 | Ivarsson et al. | |
| 5,437,840 A | 8/1995 | King et al. | |
| 5,483,346 A | 1/1996 | Butzer | |
| 5,485,277 A | 1/1996 | Foster | |
| 5,491,556 A | 2/1996 | Stewart et al. | |
| 5,573,956 A | 11/1996 | Hanning | |
| 5,593,130 A | 1/1997 | Hansson et al. | |
| 5,633,724 A | 5/1997 | King et al. | |
| 5,641,640 A | 6/1997 | Hanning ............ 435/7.92 |
| RE35,716 E | 1/1998 | Stapleton et al. ........... 435/3 |

(Continued)

FOREIGN PATENT DOCUMENTS

AU       742417      2/2000

(Continued)

OTHER PUBLICATIONS

Tadashi Saitoh, et al."Optical Characterization of Very Thin Hydrogenated Amorphous Silicon Films Using Spectroscopic Ellipsometry"; Japanese Journal of Applied Physics; vol. 30, No. 11B, Nov. 1991. pp. L1914-L1916.

(Continued)

*Primary Examiner*—Hoa Q. Pham
(74) *Attorney, Agent, or Firm*—MacPherson Kwok Chen & Heid LLP; David S. Park

(57) ABSTRACT

Imaging apparatus which images the changes in height of reactive spots on the surface of a slide requires the surface roughness of the slide to be small enough to distinguish the changes in height from the roughness features of the slide.

22 Claims, 5 Drawing Sheets

U.S. PATENT DOCUMENTS

| | | | |
|---|---|---|---|
| 5,753,518 A | 5/1998 | Karlsson | |
| 5,856,873 A | 1/1999 | Naya et al. | |
| 5,922,594 A | 7/1999 | Lofas | 435/291 |
| 5,922,604 A | 7/1999 | Stapleton et al. | 436/46 |
| 5,955,729 A | 9/1999 | Nelson et al. | 250/282 |
| 5,965,456 A | 10/1999 | Malmqvist et al. | 436/514 |
| 5,972,612 A | 10/1999 | Malmqvist et al. | 435/6 |
| 6,008,010 A | 12/1999 | Greenberger et al. | 435/41 |
| 6,008,893 A | 12/1999 | Roos et al. | 356/246 |
| 6,045,996 A | 4/2000 | Cronin et al. | 435/6 |
| 6,127,183 A | 10/2000 | Ivarsson et al. | 436/34 |
| 6,140,044 A | 10/2000 | Besemer et al. | 435/6 |
| 6,143,513 A | 11/2000 | Lofas | 435/24 |
| 6,143,574 A | 11/2000 | Karlsson et al. | 436/517 |
| 6,197,595 B1 | 3/2001 | Anderson et al. | 436/180 |
| 6,200,814 B1 | 3/2001 | Malmqvist et al. | 436/52 |
| 6,207,381 B1 | 3/2001 | Larsson et al. | 435/6 |
| 6,277,330 B1 | 8/2001 | Liu et al. | |
| 6,289,286 B1 | 9/2001 | Andersoon et al. | |
| 6,475,809 B1 * | 11/2002 | Wagner et al. | 436/518 |
| 6,493,097 B1 | 12/2002 | Ivarsson | |
| 6,503,760 B1 | 1/2003 | Malmqvist et al. | |
| D472,644 S | 4/2003 | Dawson et al. | |
| 6,589,798 B1 | 7/2003 | Loefas | |
| 6,594,011 B1 | 7/2003 | Kempen | |
| D480,149 S | 9/2003 | Dawson et al. | |
| 6,698,454 B1 | 3/2004 | Sjoelander et al. | |
| 6,806,051 B1 * | 10/2004 | Ellson | 435/6 |
| 2002/0019019 A1 | 2/2002 | Hamalainen et al. | |
| 2002/0154311 A1 | 10/2002 | Ivarsson | |
| 2002/0182717 A1 | 12/2002 | Karlsson | |
| 2003/0022388 A1 | 1/2003 | Roos et al. | |
| 2003/0067612 A1 | 4/2003 | Ivarsson | |
| 2004/0002167 A1 | 1/2004 | Andersson et al. | |
| 2004/0012676 A1 | 1/2004 | Weiner et al. | |
| 2004/0023247 A1 | 2/2004 | Xu et al. | |
| 2004/0030504 A1 | 2/2004 | Helt et al. | |
| 2004/0038268 A1 | 2/2004 | Pirrung et al. | |

FOREIGN PATENT DOCUMENTS

| | | |
|---|---|---|
| WO | WO 96/08720 | 3/1996 |
| WO | WO 96/38729 | 12/1996 |
| WO | WO 97/19375 | 5/1997 |
| WO | WO 98/32002 | 7/1998 |
| WO | WO 03/056337 A1 | 7/2003 |
| WO | WO 03/102580 A1 | 12/2003 |

OTHER PUBLICATIONS

"Handbook of Optics", Michael Bass Editor in Chief, by The Optical Society of America; vol. 1; pp. 4.23, 4.24; 1995 McGraw-Hill, Inc.

Gang Jin et al. "Imaging Ellipsometry Revisited: Developments for Visualization of Thin Transparent Layers on Silicon Substrates", American Institute of Physics, Rev. Sci. Instrum., pp. 2930-2936, Aug. 1996.

Max Born et al. "Principles of Optics—Electromagnetic Theory of Propagation, Interference and Diffraction of Light", Sixth Edition, pp. 47-51 Pergamon Press.

Eggins, "Biosensors: An Introduction", pp. 112-113, 1987 John Wiley & Sons.

Danny Van Noort et al. "Monitoring Specific Interaction of Low Molecular Weight Biomolecules on Oxidized Porous Silicon Using Ellipsometry", Biosensors & Bioelectronics vol. 13, No. 3-4 pp. 439-449, 1998 Elsevier Science, S.A. Great Britain.

Gang Jin et al. "Imaging Ellipsometry for Biosensor Applications" Transducers '95. Eurosensors IX, Digest of Technical Papers vol. 2, Sessions A7-D13, Papers No. 232-496 pp. 509-512, Stockholm, Sweden, Jun. 1995.

Jinyu Wang "Waveguide Ellipsometry Biosensors: Concept and Preliminary Analysis", SPIE vol. 1648, Fiber Optical Medical and Fluorescent Sensors and Applications pp. 44-50. 1992.

Ulf Jonsson et al. "Flow-Injection Ellipsometry—An in Situ Method for the Study of Biomolecular Adsorption and Interaction at Solid Surfaces," Colloids and Surfaces. 13 (1985) pp. 333-339, 1985 Elsevier Science Publishers BV, Amsterdam, The Netherlands.

Jonsson, Ulf et al. "Biosensors Based on Surface Concentration Measuring Devices-The Concept of Surface Concentration" Progress in Colloid and Polymer Sci. vol. 70, pp. 96-100, 1985.

Ulf Jonsson et al. "Surface Immobilization Techniques in Combination with Ellipsometry" Methods in Enzymology vol. 137, Immobilized Enzymes and Cells Part D pp. 381-1351, 1988 Academic Press, Inc. Harcourt Brace Jovanovich, Publishers.

Ch Striebel et al. "Characterization of Biomembranes by Spectral Ellipsometry, Surface Plasmon Resonance and Interferometry with Regard to Biosensor Application", Biosensors & Bioelectronics 9, pp. 139-146, 1994 Elsevier Science Publishers Ltd.

Haken Nygren et al. "Determination by Ellipsometry of the Affinity of Monoclonal Antibodies", Journal of Immunological Methods, 92, pp. 219-225, 1986 Elsevier Science Publishers Ltd.

John F. Place et al. "Opto-electronic Immunosensors: A Review of Optical Immunoassay At Continuous Surfaces", Biosensors 1, pp. 321-353. 1985 Elsevier Applied Science Publishers Ltd., England.

A. Brecht et al. "Biosensors: Fundamentals, Technologies and Applications" GBF Monographs, vol. 17, pp. 174-178, 1991 Germany.

T.A. Ruzgas et al. Ellipsometric Immunosensors for the Determination of γInterferon and □ Human Serum AlbuminŽ Biosensors & Bioelectronics 7, pp. 305-308, 1992 Elsevier Science □ Publishers Ltd.

Clifford C. Hoyt et al. "Structural analysis with quantitative birefringence imaging", American Laboratory, pp. 34-42, Jul. 1999.

Dirk Honig et al. "Direct visualization of monolayers at the air-water interface by Brewster angle microscopy", J. Phys. Chem., pp. 4590 & 4592, 1991 American Chemical Society.

S. Henon et al. "Microscope at the Brewster angle: direct observation of first-order phase transitions in monolayers", Rev. Sci. Instrum. 62, (4) pp. 936-939, Apr. 1991 American Institute of Physics.

Gang Jin et al. "A biosensor concept based on imaging ellipsometry for visualization of biomolecular interactions", Analytical Biochemistry 232, pp. 69-72, 1995.

Pentti Tengvall et al. "Complement activation by 3-mercapto-1,2-propanediol immobilized on gold surfaces", Biomaterials vol. 17, No. 10 pp. 1001-1007, 1995 Elseviar Science Ltd., Great Britain.

H. Arwin "Spectroscopic ellipsometry and biology: recent developments and challenges", Thin Solid Films 313-314, pp. 7640774, 1998 Elsevier Science S.A.

Christopher Palmer "Diffraction Grating Handbook", pp. 35-44, 2000 Richardson Grating Laboratory, Rochester, New York.

Erwin G. Loewen "Diffraction Gratings, Ruled and Holographic", Applied Optics and Optical Engineering, vol.

IX, pp. 33-71, Bausch and Lomb, Inc., Rochester, New York 1983 Academic Press, Inc.

"Optical Characterization of Very Thin Hydrogenated Amorphous Silicon Films Using Spectroscopic Ellipsometry"; by Saitoh; Hori; Suzuki; & Iida; Japanese Journal of Applied Physics; 1991.

"Handbook of Optics", by The Optical Society of America; vol. 1; pp. 4.23, 4.24; 1995.

"Imaging Ellipsometry Revisited: Developments for Visualization of Thin Transparent Layers on Silicon Substrates", by Gang Jin, et al., Rev. Sci. Instrum., pp. 2930-2936, 1996.

"Principles of Optics—Electromagnetic Theory of Propagation, Interference and Diffraction of Light", by Max Born & Emil Wolf, Sixth Edition, pp. 47-51.

"Biosensors: An Introduction", by Brian R. Eggins, pp. 112-113, 1987.

"Monitoring Specific Interaction of Low Molecular Weight Biomolecules on Oxidized Porous Silicon Using Ellipsometry", byD. Van Noort; S. Welin-Klintstrom, et al., Biosensors & Bioelectronics vol. 13, pp. 439-449, 1997.

"Imaging Ellipsometry for Biosensor Applications", by Gang Jin, et al., Transducers '95.Eurosensors IX, pp. 509-774, 1995.

"Waveguide Ellipsometry Biosensors: Concept and Preliminary Analysis", SPIE vol. 1648, by Jinyu Wang, pp. 44-50, 1992.

"Flow-Injection Ellipsometry—An In Situ Method for the Study of Biomolecular Adsorption and Interaction at Solid Surfaces", by Ulf Jonsson, et al., Colloids and Surfaces, pp. 333-339, 1985.

"Biosensors Based on Surface Concentration Measuring Devices—The Concept of Surface Concentration", by Ulf Jonsson, et al., Progress in Colloid and Polymer Sci. 70, pp. 96-100, 1985.

"[34] Surface Immobilization Techniques in Combination With Ellipsometry", by Ulf Jonsson, et al., Methods in Enzymology vol. 137, pp. 381-1351, 1988.

"Characterization of Biomembranes by Spectral Ellipsometry, Surface Plasmon Resonance and Interferometry With Regard to Biosensor Application", by Ch. Striebel, et al., Biosensors & Bioelectronics 9, pp. 139-146, 1994.

"Ellipsometric Immunosensors for the Determination of Y-Interferon and Human Serum Albumin", by T.A. Ruzgas, et al., Biosensors & Bioelectronics 7, pp. 305-308, 1992.

"Determination by Ellipsometry of the Affinity of Monoclonal Antibodies", by Haken Nygren, et al., Journal of Immunological Methods, 92, pp. 219-221, 1986.

"Opto-Electronic Immunosensors: A Review of Optical Immunoassay at Continuous Surfaces", by John F. Place, et al., Biosensors 1, pp. 321-353, 1985.

Biosensors: Fundamental, Technologies and Applications, by A. Brecht, et al., edited by F. Sche et al., GBF Monographs vol. 17, pp. 174-178, 1991.

"Kinetics of Antibody-Binding to Surface-Immobilized Antigen: Influence of Mass Transport on the Enzyme-Linked Immunosorbent Assay (ELISA)", by Nygren & Stenberg, Jour of Colloid and Interface Science, vol. 107, pp. 560-566, 1985.

"Monitoring Specific Interaction of Low Molecular Weight Biomolecules on Oxidized Porous Silicon Usiing Ellipsometry", byD. Van Noort; S. Welin-Klintstrom, et al., Biosensors & Bioelectronics vol. 13, pp. 439-449, 1997.

"Effects of Hydrophilization and Immobilization on the Interfacial Behavior of Immunoglobulins", by Martin Malmsten, et al., Journal of Colloid and Interface Science 177, pp. 70-78, 1994.

"Temporal Studies on the Deposition of Complement on Human Colostrum IgA and Serum I; Immobilized on Methylated Silicon", by Pentti Tengvall, et al., Journal of Biomedical Materials Research, vol. 35, pp. 81-91, 1997.

"Assembly of Antibodies in Lipid Membranes for Biosensor Development", by Huaiyou Wang et al., Applied Biochemistry and Biotechnology, pp. 163-181, 1994.

"Wetting and Dewetting of Si/SiO2-Wafers by Free and Lipid-Monolayer Covered Aqueous Solutions Under Controlled Humidity", by G. Elender, et al., Journal de Physique II, pp. 455-479, 1994.

"Coupling of Biomolecules to Silicon Surfaces for Use in Ellipsometry and Other Relate; Techniques", by Carl Fredrik Mandenius, et al., Methods in Enzymology, vol. 137, pp. 388-394, 1988.

"Patterning of Immobilized Antibody Layers Via Photolithography and Oxygen Plasma Exposure", by A.W. Flounders, et al., Biosensors and Bioelectronics vol. 12, pp. 447-456, 1997.

"A Comparative Study of Protein Immobilization Techniques for Optical Immunosensors", by A. Ahluwalia, et al., Biosensors and Bioelectronics 7, pp. 207-214, 1991.

"Universal Imaging Corporation—Metapolscope"; "Metamorph Imaging System", by Dr. Rudolf Oldenbourg, pp. 1-2.

"A New View on Polarization Microscopy", by Rudolf Oldenbourg, Nature vol. 381, pp. 811-812, Jun. 27, 1996.

"Structural Analysis With Quantitative Birefringence Imaging", by Clifford C. Hoyt, et al., American Laboratory, pp. 34-42, Jul. 1999.

"Direct Visualization of Monolayers at the Air-Water Interface by Brewster Angle Microscopy", by Dirk Honig, et al., J. Phys. Chem., pp. 4590 & 4592, 1991.

"Microscope at the Brewster Angle: Direct Observation of First-Order Phase Transitions in Monolayers", by S. Henon, et al., Rev. Sci. Instrum. 62, pp. 936-939, 1990.

"A Biosensor Concept Based on Imagiing Ellipsometry for Visualization of Biomolecular Interactions", by Gang Jin, et al., Analytical Biochemistry 232, pp. 69-72, 1995.

"Complement Activation by 3-Mercapto-1,2-Propanediol Immobilized on Gold Surfaces", by Pentti Tengvall, et al., Biomaterials 17, pp. 1001-1007, 1995.

"Spectroscopic Ellipsometry and Biology: Recent Developments and Challenges", by H. Arwin, Thin Solid Films 313-314, pp. 764-774, 1998.

"DNA Microarrays A Practical Approach" Edited by Mark Schena, Department of Biochemistry, Beckman Center, Standord University Medical Center, Standord, USA, Oxford University Press, 1999.

"Microarray Biochip Technology" by Mark Schena, PhD, TeleChem Internation, Inc., Sunnyvale, California, USA, A BioTechniques Books Publication, Eaton Publishing, 2000.

"Spectroscopic Ellipsometry and Reflectometry A User's Guide" by Harland G. Tompkins, Motorola Inc., and William A. McGahan, Nanometrics, Inc., A Wiley-Interscience Publication, John Wiley & Sons, inc., 1999.

"Handbook of Optics, vol. 1, Section 41.10".

* cited by examiner

APPARATUS INCLUDING A BIOCHIP FOR IMAGING OF BIOLOGICAL SAMPLES AND METHOD

REFERENCE TO RELATED APPLICATIONS

This application is a Continuation-in-Part of application Ser. No. 09/614,503 filed on 7 Jul. 2000 now U.S. Pat. No. 6,594,011 the content of which is incorporated by reference herein. This application is based in part on Provisional Patent Application Ser. No. 09/614,503 filed on 27 Oct. 2000 the content of which is incorporated by reference herein.

FIELD OF THE INVENTION

This invention relates to imaging techniques in conjunction with total internal reflection at the boundary of an optically transparent material and more particularly to the use of such techniques for detecting the presence, composition, quantity, and spatial distribution of substances on optically transparent substrates.

This invention relates to a biochip (also referred to as gene chip, protein chip, microarray and others) useful in applications of the ans caused the local polarization change detected in the respective parts of the emerging light beam. U.S. Pat. No. 5,633,724 to Ring, et al. (1997) describes the readout of a biochemical array using the evanescent field. This patent focuses on fluorescent assays, using the evanescent field to excite fluorescent markers attached to the substances to be detected and analyzed. The attachment of fluorescent markers or other molecular tags to the substances to be detected on the surface requires an additional step in performing the measurement, which is not required in the current invention. The patent further describes use of a resonant cavity to provide on an evanescent field for exciting analytes.

The formation of an array of biologically active spots on the surface of a substrate for identifying constituents in test material brought into contact with the array is well known. Typically, such processes require spots of, for example, oligonucleotides, DNA clones, antibodies, peptides, receptors, enzymes, inhibitors, etc. which are processed to exhibit fluorescence, electroluminescence, current change, voltage change—etc. for providing a detectable signature for the presence of constituents in the material being tested.

SUMMARY OF THE INVENTION

In accordance with the principles of this invention, light from a light source member providing an extended, polarized light beam is directed through a transparent substrate and undergoes total internal reflection at the surface of the substrate by a single reflection within the TIR member. The reflected light is detected by a polarization-sensitive, two-dimensional array detector. The changes of the local polarization state in the beam's cross-section caused by the total internal reflection are employed to obtain information about the presence and composition in an array of substances on the substrate surface for each point of the surface. Total internal reflection is described in; M. Born, et al., "Principles of Optics", 6th ed., pp 47–51, Pergamon Press, Oxford, 1991. In accordance with one aspect of the invention, the light generating element within the light source member is a quasi-monochromatic light source of moderate bandwidth. In a preferred embodiment, the light-generating element within the light source member is an LED of moderate bandwidth. The light from the light source member is directed through an internal reflection member to reflect off a specimen. The total internal reflection at any point within the cross-section of the light beam causes a phase shift between the light component polarized in the plane of incidence and the component polarized perpendicular to the plane of incidence. The reflected light is detected by a polarization-sensitive, two dimensional array detector and the signal from this detector is then processed in a computer to provide two-dimensional information about substances on the surface of the specimen. Spatially distributed changes in polarization state in the cross-section of the reflected beam are indicative of the substances in the specimen in the location in the specimen array corresponding to a position in the detector. The apparatus and method is especially adapted for imaging material in an aqueous solution. It is furthermore particularly suited for detecting attachment and detachment of analytes to a two-dimensional biomolecular array positioned on the total internal reflection member as part of a biosensor system. In various applications a plurality of discrete specimen spots are presented in an array, where the method and apparatus will image the array so as to distinguish each of the discrete specimen spots by an image which represents the change in polarization state within each of the discrete specimen spots. Fluorescence or molecular tagging is not necessary nor practical for use in this invention.

Further, in accordance with the principles of this invention, the apparatus disclosed in the above-identified parent application provides an image of an entire array on a biochip or if desired a portion of the entire array.

The biochip slides used in accordance with the principles of this invention must have a roughness low enough to permit separate resolution of all of the spots on the array being imaged. The apparatus disclosed allows imaging at a level of greater precision such that, a lower degree of roughness on the surface of the biochip slide is required in order to make available the more precise information.

The image information comprises height and surface coverage information of the interaction which occurs, for example, between DNA or mRNA, the oligonucleotides deposited at each location in the biochip array and the constituent in the test material flowed over the biochip array. The height of such molecules as are found in bio-arrays can be as much as 300 Å–500 Å. Some biomolecules will have a height of lesser dimension. Consequently, the surface of the substrate on which the spots are located has to have a roughness of less than about 300 Å in the measured area in order to avoid obscuration of the height information. Such precision is about equal to that of polished silicon wafers which cannot be used in the apparatus disclosed herein because silicon is not transparent. Roughness is a known unit of measure which is defined in Optical Society of America Handbook of Optics, Second Edition, volume 1, section 41.10.

Slides with such roughness characteristics used with the apparatus herein for biological testing are considered a significant departure from the prior art.

DETAILED DESCRIPTION

Figure 1:
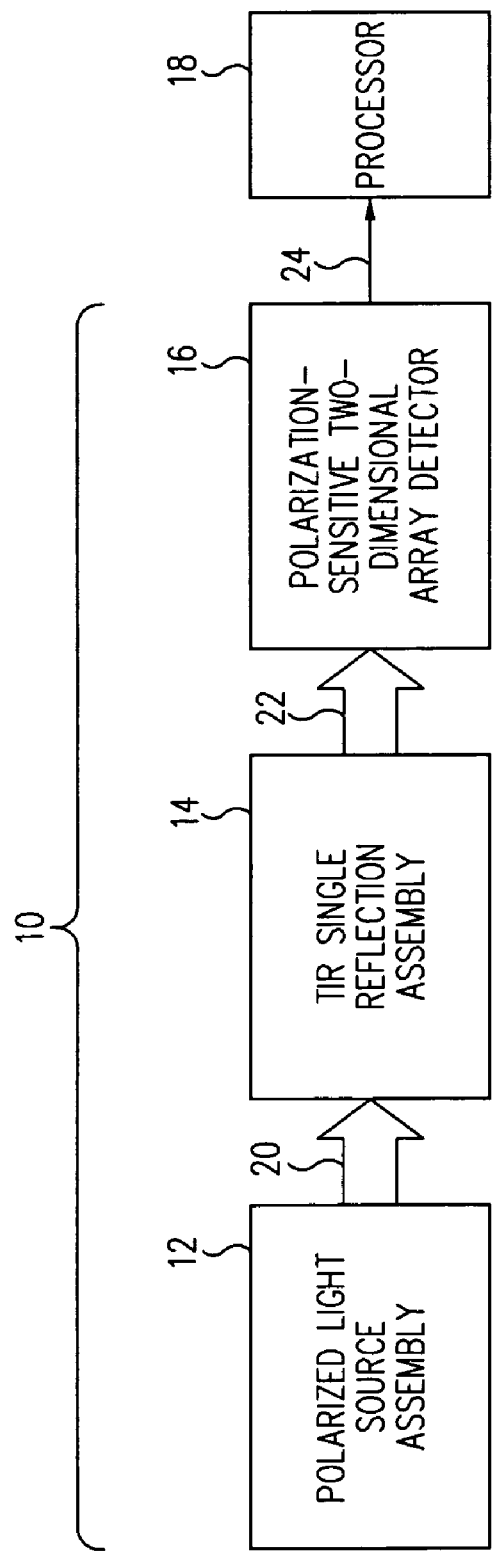
FIG. 1 is a block diagram of the invention.

The invention comprises a method and apparatus for analyzing a two-dimensional arrangement of chemical substances with an imaging technique. A polarized light source of known polarization state is directed into a total internal reflection member (TIR member) configured for a single reflection at a total internal reflection surface (TIR surface) and then exiting the TIR member. In the context of this document, superposition of reflections as encountered at a layered optical structure where the layer thicknesses are smaller than the coherence length of the illuminating light is referred to as a single reflection. The chemical specimen is in place above the TIR surface in the evanescent field of the reflected light beam. After reflection, the beam is passed to a polarization-sensitive two-dimensional detector such as a polarizer and a camera. The beam's content can then be processed to determine the change in polarization state, locally in the two-dimensional cross-section of the beam. This provides a spatially distributed map of change of polarization state in the specimen. A variety of techniques are available to determine the change in polarization such as measuring the deviation from a null condition or by comparing the input polarization state to the output polarization state. The refractive index composition of the materials within the evanescent field determines the change in the polarization state of the beam due to the reflection at the TIR surface. A two-dimensional variation of this composition within the TIR surface is associated with a respective variation of the polarization state spatially distributed across the cross-section of the reflected light beam.

In one application, the chemical specimen forms a two-dimensional array of molecules (here referred to as receptors) with specific affinities towards respective other molecules (here referred to as ligands). In this application, the invention is utilized to indicate the presence or absence of binding between ligands and receptors on the array. Such arrays commonly consist of a plurality of discrete specimen spots. The present method and apparatus will image the array so as to distinguish each of the discrete specimen spots represented by the local change in polarization state in the cross-section of the reflected beam.

Subject to limitations in resolving power of the detector, the invention permits measurement of thickness and/or refractive index composition of the specimen under investigation with a very high resolution, in the sub angstrom range, spatially resolved over an entire area. The invention is particularly useful in applications where the specimen is in an aqueous solution. In a particular application, the present invention is used to determine the presence of biological agents in a solution such as in immunosensor applications by measuring their attachment to antibodies on the TIR surface in the evanescent field. In another application, the present invention is used to determine the presence and structure of nucleic acid sequences in a solution by measuring their attachment to other nucleic acid sequences on the TIR surface in the evanescent field. Described in more detail below are different embodiments of the invention.

Figure 2:
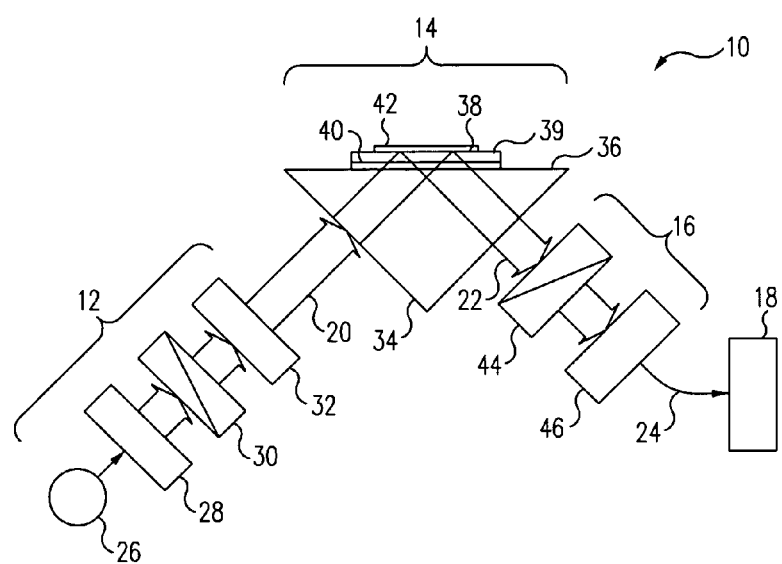
FIG. 2 is a block diagram of an embodiment of the invention.

Referring to FIGS. 1 and 2, an apparatus and method is illustrated which implements one embodiment of the invention. As shown in FIG. 1, the apparatus 10 can be described conveniently as consisting of three general portions. Portion 12 is a polarized light source assembly, portion 14 is a total internal reflection assembly providing a single reflection and portion 16 is a polarization-sensitive two-dimensional array detector assembly. Data from the detector assembly 16 is sent by an electrical signal 24 to processor 18 such as a specially programmed computer and user access system such as a print-out or image display. Data can be presented as an image, a data table, or in other forms. The polarized light source assembly 12 passes polarized light of known polarization state (which may be varied or varying) 20 to the total internal reflection assembly 14 where a single reflection occurs and the reflected light 22 having a changed polarization state passes to the detector assembly 16, where it is recorded spatially over the cross-section of the beam. The recorded data is sent to the processor 18 where the change of polarization state is determined to provide a spatially resolved map of changes in polarization state. Where the specimens are presented as an array of discrete spots, each spot will be imaged for its change in polarization state within the spot area.

FIG. 2 shows a more detailed preferred embodiment. The polarized light source assembly 12 has a light source 26, a beam forming member 28 (if the nature of the light source is such as to make beam forming useful or necessary) a polarizer 30 and an optical retarder 32. The total internal light reflection assembly 14 has an optical element 34 which has an optical surface 36. Also shown is a specimen slide 38 on the optical surface 36, and between them an index matching substance 40. Because of the index matching a total internal reflection surface (TIR surface) is defined as the upper surface 39 of the specimen slide 38. A specimen 42 is on the total internal reflection surface 39 of the slide 38. The optical element 34 is a prism configured along with the index-matched slide 38 in relationship to the incoming light beam 20, and the exiting light beam 22 such that the beam reflects only a single time at the TIR surface 39 and then exits the prism. If the specimen is placed directly on the optical surface 36, then the optical surface 36 would be the TIR surface. But this is not the usual application as the specimen (such as a biochip) is usually prepared more conveniently on a specimen slide 38 and placed in the apparatus. In any event, however constructed, there is an optical structure having a TIR surface and the beam reflects only a single time at the TIR surface between entering and leaving the optical structure. In other words, there is a TIR surface in optical contact with the specimen, such that the evanescent field associated with the total internal reflection interacts with the specimen, and there is only a single reflection at that TIR surface.

The post reflection detector assembly 16 has a polarizer 44, and a two-dimensional array detector 46, preferably a camera of the CCD type. The processor 18 is a specially programmed computer and output means for processing the imagery into a representation of film thickness variations spatially resolved over the cross-section of the area imaged.

The imaging is acquired by detecting changes spatially distributed in the local polarization state in the beam's cross-section caused by the total internal reflection. This provides information about the presence and composition in the array of substances on the substrate surface for each resolvable point on the surface. Different polarization state changes are included in the cross-section of the reflected beam indicative of the substances on the specimen in the location in the specimen array corresponding to a position in the detector. The processor 18 receives the data as an electrical signal 24 and characterizes the change of polarization state spatially over the two-dimensional array. In the processor 18, the analysis and processing is done in one embodiment by comparing the known polarization state of the incoming light from the light processing assembly 12 with the changed polarization state of the reflected light 22, spatially resolved two-dimensionally within the beam which provides a map of spatially distributed points or spots in the specimen array. The polarization shift is then analyzed by the processor 18 to provide information of the presence and properties of elements in the chemical specimen. Other known techniques, such as null processing can be used to determine the change in polarization state.

Alternatively, the light source member 26 may be an LED, an SLD (Super Luminescent Diode), an incandescent light source, or a laser. If an LED or SLD is used, the set-up shown in FIG. 2 is appropriate, where the beam-forming member 28 is a collimator. If an incandescent light source is used, an optical filter is also used.

In one embodiment, the light source 26 for the apparatus is a quasi-monochromatic light source of moderate bandwidth. In accordance with the invention the light source 26 is preferably an LED of moderate bandwidth. Preferably the bandwidth is a full width half maximum wavelength in the range of about 10 nm–50 nm, and more preferably a full width half maximum wavelength in the range of about 30nm–50nm.

Referring to the optical retarder 32 as shown in FIG. 2, in an alternative embodiment, the optical retarder could be placed instead in the exiting beam path 22 before the polarizer 44.

Figure 3:
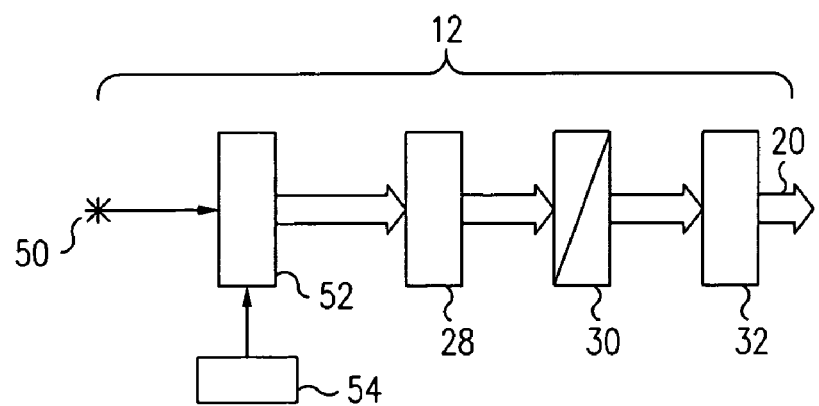
FIG. 3 is a block diagram of alternative portions of the invention.

Referring to FIG. 3, an alternative embodiment is shown. When the light source is a laser 50, a moving diffuser 52 is adapted to produce speckle-offsetting fluctuation of the minima and maxima in the speckle pattern caused by the laser. The moving diffuser 52 is attached to a mechanical actuator 54 which is preferably a motor and servo-apparatus for providing the speckle offsetting fluctuations. The beam 20 then proceeds through the beam-forming element 28, the polarizer 30 and the optical retarder 32, exiting the light source assembly 20.

The polarizer 30 employs a polarizer of selected known polarization state. The polarizer 30 may be of the type having a mechanical actuator driven by a motor control signal so as to enable varying and selecting the polarization state of the light beam 20.

As mentioned above, the total internal reflection optical element 34 either alone or in combination with an index matched slide may be arranged for use with a specimen in various ways to define a total internal reflection assembly so long as the specimen is in the evanescent field of the reflected beam 20,22.

As noted above, the specimen 42 could be set directly on the optical surface 36 in which case the optical surface 36 would be the TIR surface but this is inconvenient and repeated use is likely to degrade the optical quality of the optical surface 36, and therefore, consistent with common practice in which a biochip or other chemical assay specimen is provided, a specimen slide 38 or other supporting apparatus is employed. It is common in a biochip to provide an array of discrete specimen spots supported on a structure for obtaining analysis of each spot. The term total internal reflection optical element refers to known optical elements alone or in combination with other elements which provide the phenomenon known as total internal reflection. FIG. 2 shows use of a prism combined with a slide 38, being index matched so that there is a TIR surface 39.

Figure 4:
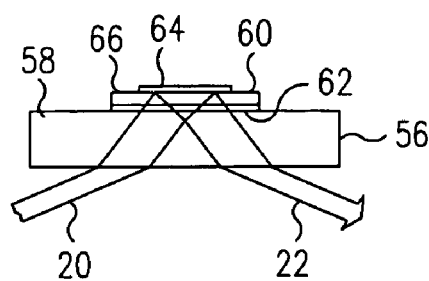
FIG. 4 is a block diagram of alternative portions of the invention.
Figure 5:
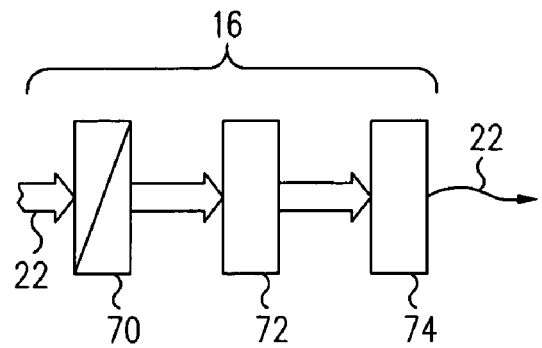
FIG. 5 is a block diagram of alternative portions of the invention.

FIG. 4 shows an alternative optical arrangement in which a flat optical member 56 having an upper surface 58 is surmounted by a specimen slide 60 and an index matching substance 62 on which is a specimen 64. The TIR surface 66 is the top of the slide 60. The beam 20 enters the assembly, is refracted as it enters, and leaves the optical member 56 after a single reflection at the TIR surface 66 as beam 22. Other mechanisms for providing total internal reflection and an evanescent field can be employed in practicing this invention as long as only a single reflection occurs at the TIR surface upon which the specimen is placed so as to be in the evanescent field associated with the reflection. As seen in FIG. 5, the post-reflection processing arrangement 16 through which the beam 22 passes, can alternatively, consist of a polarizer member 70, a beam forming member 72 and a two-dimensional array detector 74.

The method and apparatus can be used in combination with biochips of the type having discrete specimen spots or a micro-titer plate containing an array of discrete spots or locations for analysis, where the detected change in polarization state is spatially related to the discrete locations in the reflected beam. Therefore, as used herein the slide and specimen refers to any type of chemical or biological array which is desired to be examined.

The foregoing described apparatus and methods are especially beneficial for imaging materials in an aqueous medium.

The invention as described above provides an extremely sensitive optical imaging system for real-time imaging of the binding status of biochip array elements on the surface of a glass or plastic chip. An exemplary monitored array spot is approximately 25 mm in diameter, with a lateral resolution better than 10 microns, resulting in fully parallel, continuous real-time readout of up to 5 million sensor fields. Sensor sensitivity to surface attachment is in the femtogram/mm$^2$ range (e.g. one DNA per square micron) and spatial resolution of 20 microns.

The apparatus of FIG. 1 operates by imaging the pattern of reaction results on the biochip. Those reactions produce changes in the height of the resulting material which react at each spot, imaging an area of array containing numerous spots. The area imaged could be a portion or the entire biochip array. By providing an array of spots of different materials, different constituents in test material flowed over the spots bind in a manner which identifies those constituents. By including in a computer memory the positions of the various materials in the different spots of the array, the image produced by the apparatus of FIG. 1 not only identifies the constituents in the test material, but also can determine the rate at which the reactions occur and the height of the resulting molecules at each spot. With the apparatus described height differences can be imaged dynamically over such short periods of time that intermediate height change readings can be recorded and therefore height change rate can be determined as well as allowing comparison of the rate of height change or intermediate amount of height change among the for spots on the biochip array.

In certain types of biochip analysis the height of molecules on the spots is on the order of 300 Å to 500 Å (Å=angstrom). Accordingly, the surface of a slide on which the spots are formed should have a maximum roughness of less than about 300 Å in the measured area in order to avoid the loss of information in the resulting image. This is particularly applicable to hybridization arrays of target nucleic acid and oligonucleotide arrays. For better imaging resolution, the slide roughness should be about 50% or less than the height of molecules on the spots. Roughness is a known unit of measure which is defined in Optical Society of America, Handbook of Optics, Second Edition, Volume I, section 41.10.

Figure 6:
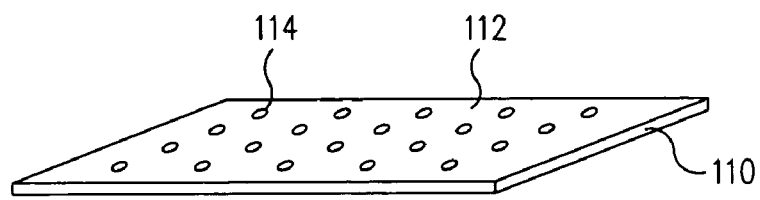
FIG. 6 is a schematic projection view of a biochip useful in the apparatus of FIG. 1.

In certain applications it is desirable that the surface roughness be less than the change in height caused by the binding reaction. FIG. 6 is a schematic projection view of a slide suitable for use in the apparatus of FIG. 1-5. The slide 110 has a top surface 112 on which an array of spots 114 is formed.

Figure 7:
FIG. 7 is a schematic view of the slide of FIG. 2 showing a representative spot.
Figure 8:
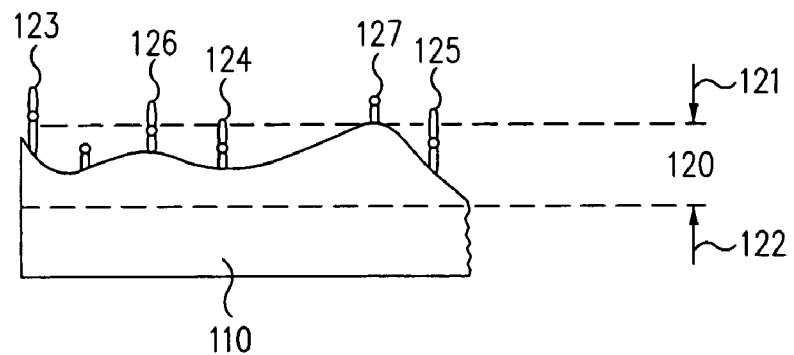
FIG. 8 is an hypochetrial enlarged view of a biochip of the prior art representing the surface roughness of the slide and biomolecules.

FIG. 7 is a side view of the slide of FIG. 6 illustrating a representative spot 116. FIG. 8 is an enlarged portion of a slide of FIG. 6 illustrating a plurality of spots after interaction in the context of an exaggerated surface roughness for the slide as in the prior art. The horizontal broken line 120 represents the maximum surface roughness as indicated by the opposing arrows 121 and 122. It can be seen from the figure that the height of a reacted spot at 123 is exaggerated as compared to a reacted spot at 124 and at 125. Similarly, unreacted spots at 126 and 127 distort the resulting image where they should provide an equal result.

Figure 9:
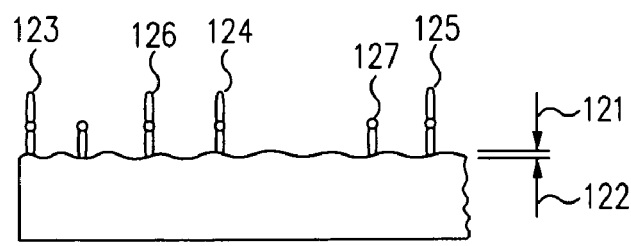
FIG. 9 is an enlarged schematic side view of a biochip slide having reduced roughness in accordance with the principles of the invention.

FIG. 9 illustrates the point by showing the same interaction pattern where the surface roughness is less than a small portion of the height of the molecule produced by a reaction at each spot. Like numerals are used in FIGS. 8 and 9 to facilitate comparisons between the two figures.

Figure 10:
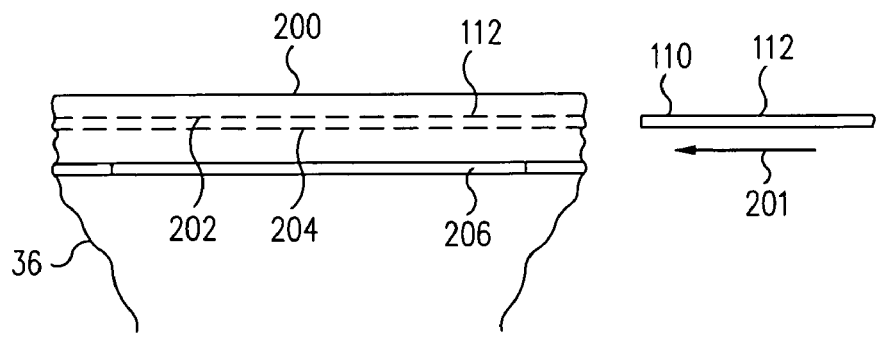
FIG. 10 is a schematic representation of a jig for holding the slide of FIG. 2.

In practice, the slide of FIG. 6 is positioned in a fixture 200 as shown in FIG. 10. The slide is inserted into the fixture by movement as indicated by the arrow 201, into a position represented by horizontal dashed lines 202 and 204. The slide is spaced apart from surface 36 of optical element 34 of FIG. 1. The spacing between surface 36 and the opposed bottom surface of the slide contains a fluid 206 of a matching index of refraction which, for all practical purposes, renders those surfaces invisible and providing for TIR only from the top surface 112 of the slide 10.

The biochip of FIG. 6 can include an array, for example, of 100,000 spots and those spots can be imaged simultaneously or in selected sub-arrays. Each spot has a diameter of from 50 microns to 500 microns where each spot comprises a biological element (i.e. oligonucleotides, cDNA clone, protein, antibody, antigen, bacteria, enzyme, inhibitor, receptor and others). Each spot has a known designation for, for example, genes for breast cancer, prostate cancer, aging and others,—(up to 80,000 genes). The biological elements must be substances that can be attached by various chemical and physical techniques to create a biochip. A full discussion of biochip fabrication is included in "Microarray Biochip Technology" by Mark Schena, a Biotechniques Books Publication, 2000. "DNA Microarrays: A Practical Approach" by Mark Schena, a Practical Approach Series, 2000.

The binding status of biological array elements (spots) on the surface of a (glass) slide or chip is obtained by the apparatus of FIG. 1. The slide monitoring area is approximately 25 mm in diameter with a lateral resolution better than 10 microns, resulting in fully parallel, continuous, real-time readout of up to five million sensor fields. System sensitivity to surface attachment is in the femtogram/mm$^2$ range. The apparatus and chip have application to DNA and protein chip scanning, high throughput screening, ligand fishing, immunosensors, clinical diagnostics and research, toxicology profiling, binding kinetics research, genomics and protemics. Particular features include; real-time imaging, no labels necessary, sensitivity of 1 fg/mm$^2$ (one DNA per square micron), partial resolution of 20 microns, and a sensor field of about 24 mm diameter.

Figure 11:
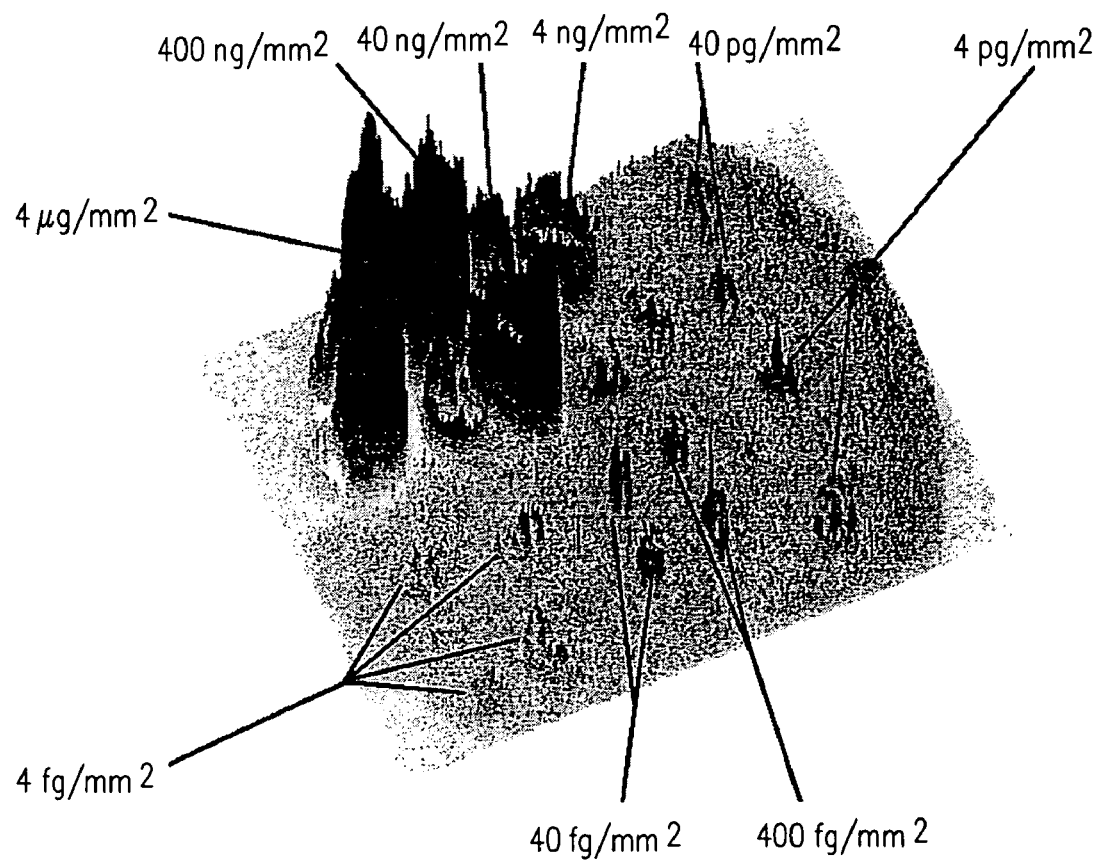
FIG. 11 is a computer printout of an area plot of spots of a microarray.

The above described imaging apparatus was used to measure the thickness of protein layers deposited directly on the prism surface, which has a surface roughness of $\lambda$/10. Tests were performed by depositing small droplets (~0.5 mm in area, 200 nl in volume) of bovine serum albumin (BSA) solutions directly on the sensor surface (the TIR surface). After the water was evaporated, only the protein remained on the surface leaving a well-defined quantity of protein at the test location. Table 1 lists the number of molecules per drop for each concentration, as well as an estimate of the effective layer thickness based on the area the droplet covered on the surface. The intensities as measured by a CCD camera detector for the surface was computer plotted as an area plot and is shown in FIG. 11. From this figure, it can be seen that with an increase in the concentration of protein the signal increases. The plot readily distinguishes each spot. Very small measurements were detected. In particular, a thickness change of as little as 10 fm was detected and was distinguished from background noise. Consequently, with such sensitivity, in order to be able to exploit the increased precision measurement available from the apparatus, the surface roughness of the support element of the microarray must be reduced.

TABLE 1

BSA dilutions and molecular quantities in sample droplets

| Concentration | BSA mass per drop | BSA Molecules/ drop | Moles per drop | Number of Molecular Layers | Effective Film thickness | Protein coverage |
| --- | --- | --- | --- | --- | --- | --- |
| 10 mg/ml | 2 μg | 1.8 *10$^{13}$ | 30 pmol | 400 | 10 μm | 4 μg/mm$^2$ |
| 1 mg/ml | 200 ng | 1.8 *10$^{12}$ | 3 pmol | 140 | 1 μm | 400 ng/mm$^2$ |
| 100 μg/ml | 20 ng | 1.8 *10$^{11}$ | 300 fmol | 14 | 100 nm | 40 ng/mm$^2$ |
| 10 μg/ml | 2 ng | 1.8 *10$^{10}$ | 30 fmol | 1.4 | 10 nm | 4 ng/mm$^2$ |
| 1 μg/ml | 200 pg | 1.8 *10$^{9}$ | 3 fmol | 0.14 | 1 nm | 400 pg/mm$^2$ |
| 100 ng/ml | 20 pg | 1.8 *10$^{8}$ | 300 amol | 0.014 | 100 pm | 40 pg/mm$^2$ |
| 10 ng/ml | 2 pg | 1.8 *10$^{7}$ | 30 amol | 1.4*10$^{-3}$ | 10 pm | 4 pg/mm$^2$ |
| 1 ng/ml | 200 fg | 1.8 *10$^{6}$ | 3 amol | 1.4*10$^{-4}$ | 1 pm | 400 fg/mm$^2$ |

TABLE 1-continued

BSA dilutions and molecular quantities in sample droplets

| Concentration | BSA mass per drop | BSA Molecules/ drop | Moles per drop | Number of Molecular Layers | Effective Film thickness | Protein coverage |
|---|---|---|---|---|---|---|
| 100 pg/ml | 20 fg | 1.8 *10$^5$ | 0.3 amol | 1.4*10$^{-5}$ | 100 fm | 40 fg/mm$^2$ |
| 10 pg/ml | 2 fg | 1.8 *10$^4$ | 0.03 amol | 1.4*10$^{-6}$ | 10 fm | 4 fg/mm$^2$ |

In the broadest sense, one aspect of invention is in a biochip having a slide whose surface, which is the TIR surface, is of sufficiently low roughness specification that an array of spots imaged by the apparatus can be individually resolved using the apparatus described above.

A process using the apparatus and a biochip of such sufficiently low roughness is:

placing the biochip surface in a flow cell in combination with the apparatus such that the surface of the slide which has the spots is the TIR surface;

initially calibrating the apparatus such that light reflected from the biochip yields a fully-linear polarization;

adjusting the analyzer to a null position to fully block the linearly polarized light. flowing target molecules over the biochip surface.

When the null position is achieved, every region where the chip (slide) surface deviates from the initial state stands out as a bright spot whose intensity is directly related to the thickness (height) differences induced by the deviation. In this process target molecules will be flowed over the biochip surface. The intensity of the biochip may be continuously monitored across the array to study thickness changes that occur on the biochip. The relative intensity measured at the detector will be related to the sample parameters and the setting of the polarizing elements using computer programs based on a detailed "Jones calculus" sensor system description. With these programs theoretical plots will be fitted to the acquired measurement data sets, and the outputs' dependence on parameter variations can be visualized. At the start of the procedure, the entire biochip is homogeneously dark. As the antibodies begin to bind to the reference probes the intensity along the surface increases. The intensity is expected to be the highest for high affinity interactions and mild changes are expected for low affinity interactions. The rate of intensity change can be related to the affinity constraints of the system. In a single procedure, the affinity measurements for multiple peptides can be performed. Moreover, the effect of binding density (because different concentrations of peptides are used in spotting) can also be measured.

What has been described is merely illustrative of the invention and many variations and modifications thereof can be devised by those skilled in the art within the spirit and scope of the invention as encompassed by the following claims.

What is claimed is:

1. Apparatus for measuring reactions on a biochip during a microarray procedure by imaging the changes in height which occur at the spots of an array of spots on a biochip, said biochip including a transparent slide having a surface on which the spots are placed, the entire surface having a surface roughness of less than the height of molecules in the spots on said surface.

2. The apparatus of claim 1 in which the slide is transparent to electromagnetic radiation in a range of wavelengths used by said apparatus to form an image of the height profile of reactions at the spots of said array.

3. The apparatus of claim 1 including a prism having a first surface said surface having a surface roughness of less than about 300 Å.

4. The apparatus of claim 1 wherein said surface roughness is sufficiently low to allow resolution of molecules in said spots.

5. The apparatus of claim 1 wherein said surface roughness is lower than the change in height after a binding reaction.

6. The apparatus of claim 1, wherein the surface roughness is sufficiently low to resolve as separate images changes in height in the femtogram/mm$^2$ range.

7. The apparatus of claim 1, wherein the surface roughness is a fraction of the biomolecule height.

8. The apparatus of claim 1, wherein the surface roughness is sufficiently low to permit distinguishing the changes in height from the roughness features of the surface.

9. A biochip including a transparent slide having a first surface, the entire surface having a surface roughness of less than about 300 Å, said surface having thereon an array of spots, each of said spots including a biological test material.

10. An apparatus for measuring reactions on a biochip by imaging the changes in height of biomolecules which occur at the spots of an array of spots on the surface of the biochip, the apparatus comprising:

an optical imaging apparatus having a polarized light source emitting a polarized, extended beam of light;

a TIR structure having a TIR surface, the light from said polarized light source member being reflected only a single time by the TIR surface, the array of spots being within the evanescent field associated with the total reflection at the TIR surface; and a polarization-sensitive, two-dimensional array detector, said detector detecting the light beam reflected from the TIR surface including the spatially distributed polarization change caused by the array of spots;

the entire TIR surface having a surface roughness of less than the height of molecules in said spots.

11. An apparatus for imaging binding reactions on a biochip by imaging the changes in height of biomolecules which occur at the spots of an array of spots on the surface of the biochip comprising a TIR surface having a surface roughness sufficiently low that spots on the bio chip can be resolved as separate images and that thickness changes can be resolved on the spots, the entire TIR surface having a surface roughness of less than the height of molecules in the spots on said surface.

12. The apparatus of claim 11 wherein said surface roughness is about 300 Å or less within the measured area.

13. Apparatus for measuring reactions on a biochip by imaging the changes in height which occurs at the spots of an array of spots on the surface of a biochip, said biochip including a transparent slide having a surface roughness sufficiently low to resolve as separate images changes in height in the femtogram/mm² range, the entire surface having a surface roughness of less than the height of molecules in the spots on said surface.

14. An apparatus for measuring binding reactions on a biochip by imaging the changes in height of biological material which occurs at the spots of an array of spots on a surface of the biochip wherein the surface roughness of said surface is a fraction of the biomolecule height, the entire surface having a surface roughness of less than the height of molecules in the spots on said surface.

15. An apparatus for measuring binding reactions on a biochip by imaging the changes in height of biological material due to the binding reactions which occur at the spots of an array of spots on the surface of the biochip wherein the surface roughness of said surface is sufficiently low to permit distinguishing the changes in height from the roughness features of the surface, the entire surface having a surface roughness of less than the height of molecules in the spots on said surface.

16. An apparatus for measuring reactions on a biochip by imaging the changes in height of biological material which occurs at the spots of an array of spots on the surface of the biochip, the apparatus comprising:
  an optical imaging apparatus having a polarized light source emitting a polarized, extended beam of light;
  a TIR structure having a TIR surface, the light from said polarized light source member being reflected only a single time by the TIR surface, the array of spots being within the evanescent field associated with the total reflection at the TIR surface; and
  a polarization-sensitive, two-dimensional array detector, said detector detecting the light beam reflected from the TIR surface including the spatially distributed polarization change caused by the array of spots;
  the TIR surface having a surface roughness that is sufficiently low to permit distinguishing the changes in height from the surface roughness features, the entire TIR surface having a surface roughness of less than the height of molecules in the spots on said surface.

17. Apparatus for spatially resolved imaging of a plurality of spots in a bioarray of spots on the surface of a biochip, the apparatus comprising:
  an optical assembly in which the biochip is a part and in which the surface is a TIR surface for an extended beam of polarized light introduced into the optical assembly, the said surface being the only TIR surface in the path of the beam of light, the entire TIR surface having a surface roughness of less than the height of molecules in the spots on said surface; and
  a source of an extended beam of polarized light positioned in relation to the optical assembly to cause the extended beam of polarized light to enter the optical assembly and to have a single total internal reflection in the optical assembly which total internal reflection occurs at the TIR surface, and thereafter exits the optical assembly.

18. The apparatus of claim 17 further comprising an image capturing device positioned to receive the beam of light exiting from the optical assembly to record the spatially resolved changes in polarization impressed on the beam of light by the plurality of spots of the bioarray which are within the area of the beam of light.

19. The apparatus of claim 17 wherein said optical assembly includes a prism having a first surface and the biochip, and the prism and the biochip are assembled such that the surface of the biochip on which the spots reside is the only TIR surface of the optical assembly in the path of the beam of light.

20. The apparatus of claim 19 wherein the biochip resides on a surface of the prism with an index matching fluid between them to cause polarized light to pass from the prism through the slide to the TIR surface and to be reflected back into the prism in a single reflection at the TIR. surface and thereafter to exit the optical assembly.

21. A method for obtaining spatially resolved images of a plurality of spots of an array of spots on a biochip surface comprising:
  placing a biochip having an array of spots on its upper surface into combination with a prism to form an optical assembly in which the upper surface of the biochip is a TIR surface and such that an extended beam of polarized light introduced into the optical assembly will have only a single reflection at the TIR surface, the entire TIR surface having a surface roughness of less than the height of molecules in the spots on said surface.

22. The method of claim 21 further comprising recording the spatially resolved images of spots on the biochip surface within the beam of light.

* * * * *